United States Patent
Bleuer

(10) Patent No.: US 6,595,352 B2
(45) Date of Patent: Jul. 22, 2003

(54) CONTAINER FOR RECEIVING A FILLING PRODUCT AND A METHOD FOR ITS MANUFACTURE

(75) Inventor: Richard Bleuer, Eichberg (CH)

(73) Assignee: Coltene AG, Alstatten (CH)

( * ) Notice: Subject to any disclaimer, the term of this patent is extended or adjusted under 35 U.S.C. 154(b) by 80 days.

(21) Appl. No.: 09/785,186

(22) Filed: Feb. 20, 2001

(65) Prior Publication Data

US 2001/0015326 A1 Aug. 23, 2001

(30) Foreign Application Priority Data

Feb. 21, 2000 (EP) .......................................... 00810143

(51) Int. Cl.⁷ .............................................. A61B 19/02
(52) U.S. Cl. ..................................... 206/63.5; 206/219
(58) Field of Search ..................... 206/63.5, 219–222, 206/565; 220/8; 215/305

(56) References Cited

U.S. PATENT DOCUMENTS

| | | | | |
|---|---|---|---|---|
| 2,416,142 A | * | 2/1947 | Bennett ...................... | 138/140 |
| 4,142,629 A | * | 3/1979 | Biondo et al. ............... | 206/219 |
| D255,714 S | * | 7/1980 | Lancellotti .................. | 206/219 |
| 4,552,266 A | * | 11/1985 | Weissenburger ............ | 206/220 |
| 4,557,376 A | * | 12/1985 | Probst et al. ............... | 206/219 |
| 4,562,979 A | * | 1/1986 | Taylor ........................... | 220/8 |
| 4,844,308 A | | 7/1989 | Porteous | |
| 5,394,980 A | * | 3/1995 | Tsai .......................... | 206/219 |
| 5,396,986 A | * | 3/1995 | Fountain et al. ............ | 206/219 |
| 5,462,875 A | * | 10/1995 | Barr et al. ................ | 435/289.1 |
| 5,622,500 A | * | 4/1997 | Niznick ...................... | 206/63.5 |
| 6,360,886 B1 | * | 3/2002 | Welsh ......................... | 206/219 |

FOREIGN PATENT DOCUMENTS

| | | |
|---|---|---|
| DE | 0 024 402 | 12/1971 |
| EP | 0 043 468 | 1/1982 |
| FR | 63921 | 10/1955 |
| FR | 1 493 708 | 7/1967 |
| FR | 70262 | 9/1967 |

* cited by examiner

Primary Examiner—Shian Luong
(74) Attorney, Agent, or Firm—Shoemaker and Mattare

(57) ABSTRACT

A container for filling a predetermined quantity of filling product, in particular pasty tooth filler masses, has a cylindrical base body with two oppositely lying hollow spaces and a connection piece lying therebetween. The hollow spaces are closable with snap lids so that hygiene and where appropriate sterility of the filling product are guaranteed.

19 Claims, 3 Drawing Sheets

Figure 1:
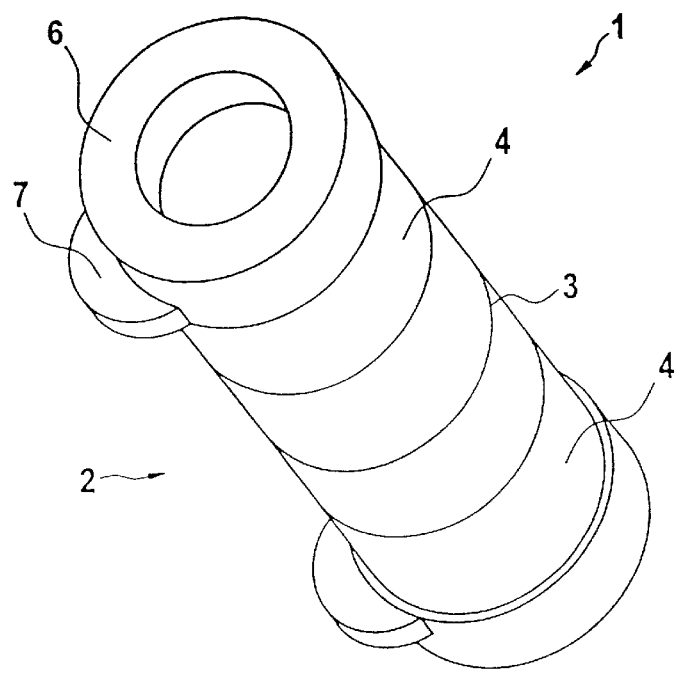

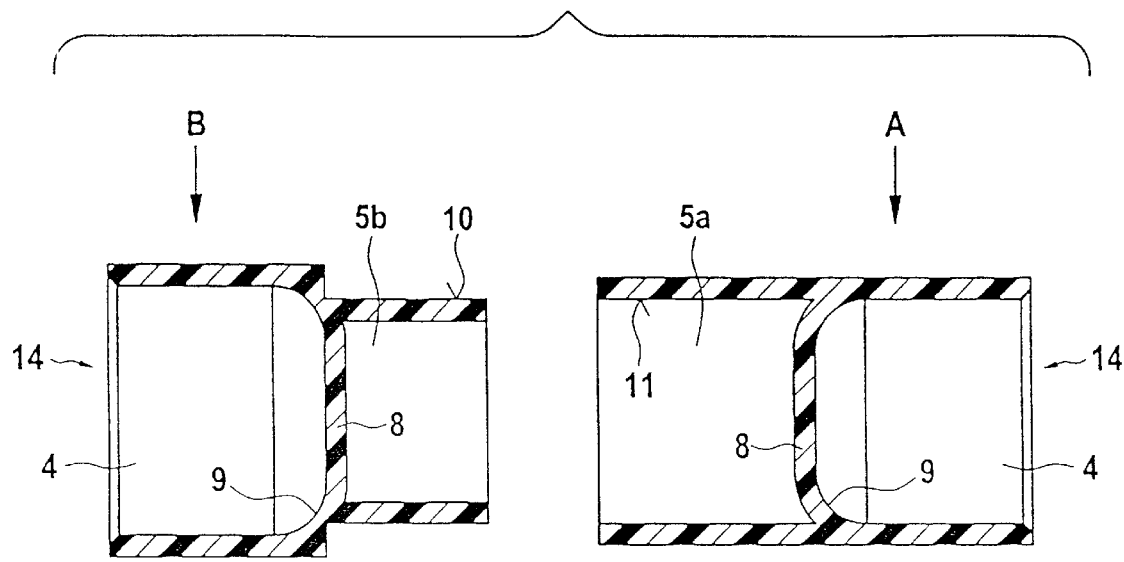
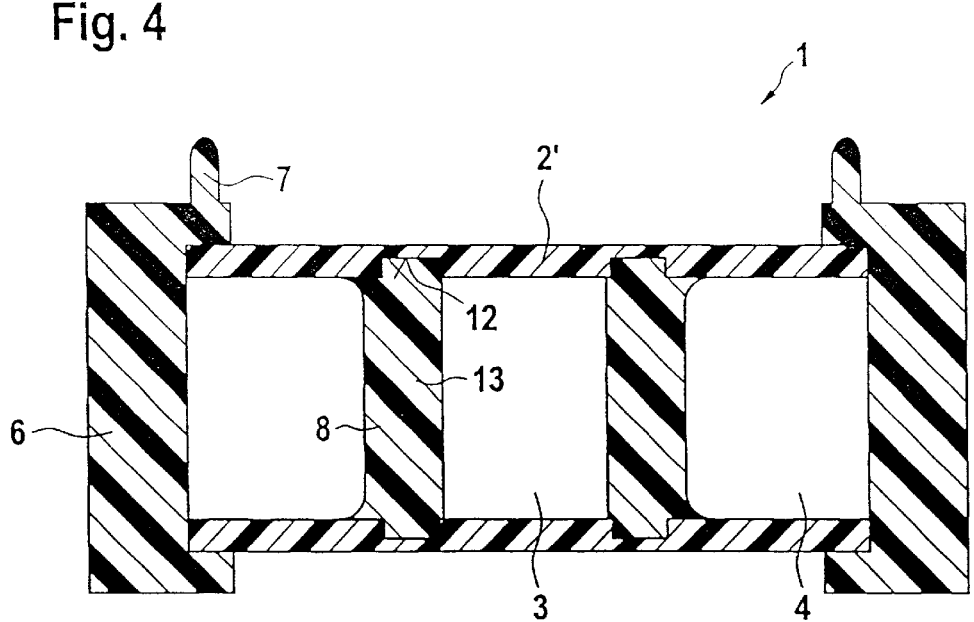

CONTAINER FOR RECEIVING A FILLING PRODUCT AND A METHOD FOR ITS MANUFACTURE

The invention relates to a container for receiving a certain quantity of a filling product, preferably for receiving pasty tooth filler masses, as well as to a method for manufacturing such a container with a filling product.

Pasty tooth filler masses are today filled up in the most varied of quantities and packagings. Thus filling quantities which are sufficient for several applications, in particular with chemically-hardening tooth filler masses, are filled up in larger tins or containers. The filler material is removed with a tool, e.g. a spatula and portioned according to application. However there are also known syringes or tubes with filled quantities for several applications which have at their disposal devices for the portioning according to application. The application of packages with filling quantities for multiple applications at the user requires a good basic turnover of the pasty tooth filler masses and creates certain demands on storage and hygiene.

Packaging forms for small volumes e.g. single portions are already known from the prior art. On account of the small volumes the handling of these filling quantities has however up to now entailed the application of technical auxiliary means. Thus e.g. small tips or cartridges are placed on a means which has at its disposal hand grips and a pressure pin, with which via an outlet the emptying procedure of the filling product from the tip or cartridge may be initiated. The application of such technical auxiliary means entails corresponding costs. The handling is awkward.

It is the object of the invention to avoid the disadvantages of the prior art, in particular to make available a simple cheap container which permits on the one hand the filling of relatively small quantities of filling product, in particular pasty tooth filler masses and on the other hand in spite of the small volumes of filling product and container, ensures an optimal handling.

In particular a simple, one-handed manipulation is to be made possible which permits the simultaneous fixing and opening of the container so that the other hand remains free for a rapid withdrawal and application of the filling product.

According to the invention this object is achieved with a container and with a method for manufacturing such a container with a filling product, according to the characterising features of the independent patent claims.

A container has a roughly cylindrical base body which comprises at least one closable hollow space for receiving a certain quantity of filling product, in particular pasty tooth filler masses, and an extension piece.

The closable hollow space permits the filling of a filling product like pasty tooth filler masses in portions which are envisaged for one or repeated applications. By way of the preferably light-tight and moisture-tight reclosable closure the hygiene and where appropriate the sterility are ensured.

In particular there are filled the light-hardening or chemically-hardening pasty tooth filler masses common today in the dental field. So that in spite of the relative small volume of the hollow space there is ensured an optimal handling, the container comprises an extension piece which does not serve for receiving filling material.

The roughly cylindrical base body of the container may be formed of a tube with through-going side walls running perpendicularly to the openings. Conceivable are however also base bodies with e.g. a polygonal cross section.

If the base body comprises two oppositely lying closable hollow spaces, two predetermined quantities of filling product may be filled and the volume of the extension piece lying therebetween may be reduced, with the dimensioning and handling ability of the container remaining the same. In a particularly preferred embodiment of the invention with two hollow spaces the extension piece has practically the same length as a hollow space.

If the outer wall of the extension piece is roughly in alignment with the outer wall of the container there may be achieved a homogeneous, well manipulatable and manufacturable base body.

For the manufacture of the container there is particularly suitable a base body which consists of two parts which are releasably or unreleasably connected to one another with a non-positive and/or positive fit. The individual parts may thus in particular be manufactured with the injection moulding method of plastics, e.g. opaque polypropylene.

In a particularly simple manner a container may be put together when the two parts each comprise a connection section, wherein the connection sections advantageously are connected to one another such that the outer wall of the connection section of the one part with a non-positive fit bears on the inner wall of the connection section of the other part.

The two parts each comprise a closable hollow space for receiving a predetermined quantity of filling product, which hollow space being separated from the respective connection section by a bottom. With this a functional compartmentisation of the base body is achieved. The bottom may be manufactured with the injection moulding method as one piece with the base body, for example of an opaque polypropylene. In particular with embodiment forms with which the bottom is only applied with a non-positive fit into the base body afterwards, there may however be applied a softer material such as e.g. polyethylene.

In a particularly preferred embodiment of the invention the bottom of the hollow spaces in each case comprises a curved transition section blending into the side walls. By way of this the complete removal of the filling product with an instrument, in particular with a spatula, is simplified. Particularly advantageous has shown to be the curved transition section in combination with a cylindrical base body.

The useable volume of the closable hollow spaces is preferably not more than max. 0.8 $cm^3$, preferably about in each case 0.2 $cm^3$ to 0.6 $cm^3$. By way of this a portioning optimal for dental application is achieved.

So that the handling of the container, in particular the holding in the hand, e.g. between the thumb and the index finger is ensured, the cylindrical base body should have a minimal length of 20 mm. Of course in practice infinitely long base bodies are not suitable. In a particularly preferred embodiment of the invention the cylindrical base body comprises a length of 27 mm and a diameter of 11 mm.

By way of a snap lid which may be placed on the base body and which is preferably closable in a light-tight and moisture-tight manner, the hygiene and where appropriate sterility of the filling product is ensured. With a snap lid a particularly simple handling, in particular simple opening is achieved.

In particular when the snap lid comprises a projection it is achieved that the container is held with one hand and may be opened with the thumb so that the filling product may be rapidly removed and applied with an instrument, for example with a spatula.

Conceivable is also that the snap lid with its whole circumference overlaps the outer wall of the cylindrical base body.

The snap lid may be manufactured of the same material as the base body, for example an opaque plastic such as polypropylene. Conceivable is also a softer plastic such as polyethylene.

A further subject-matter of the invention is an integrated system consisting of two or more containers according to the invention, wherein the individual containers are separably joined together (e.g. arranged next to one another in a row or connected to one another). Such an integrated system is particularly suitable for the storage and the transport of the relatively small container. The connection between individual containers by way of one-piece injection or later adhesing may be designed such that the containers which are used individually may be particularly easily separated from one another, e.g. by twisting.

A further subject-matter of the invention is a method for manufacturing and filling a container according to the invention which comprises a preferably cylindrical base body with two hollow spaces for receiving a predeterminable quantity of filling product. Characteristic for the method is that two parts with in each case a hollow space are prepared and subsequently connected to one another, so that there arises a container with two oppositely lying hollow spaces. The hollow spaces before or after the connecting are filled with a predermined quantity of filling product, in particular with pasty tooth filler masses.

Preferably the method is carried out such that the two prepared parts are firstly filled and closed and only subsequently connected to one another. By way of this a rotation during the filling procedure which would be necessary with an already put together container may be avoided.

Figure 2:
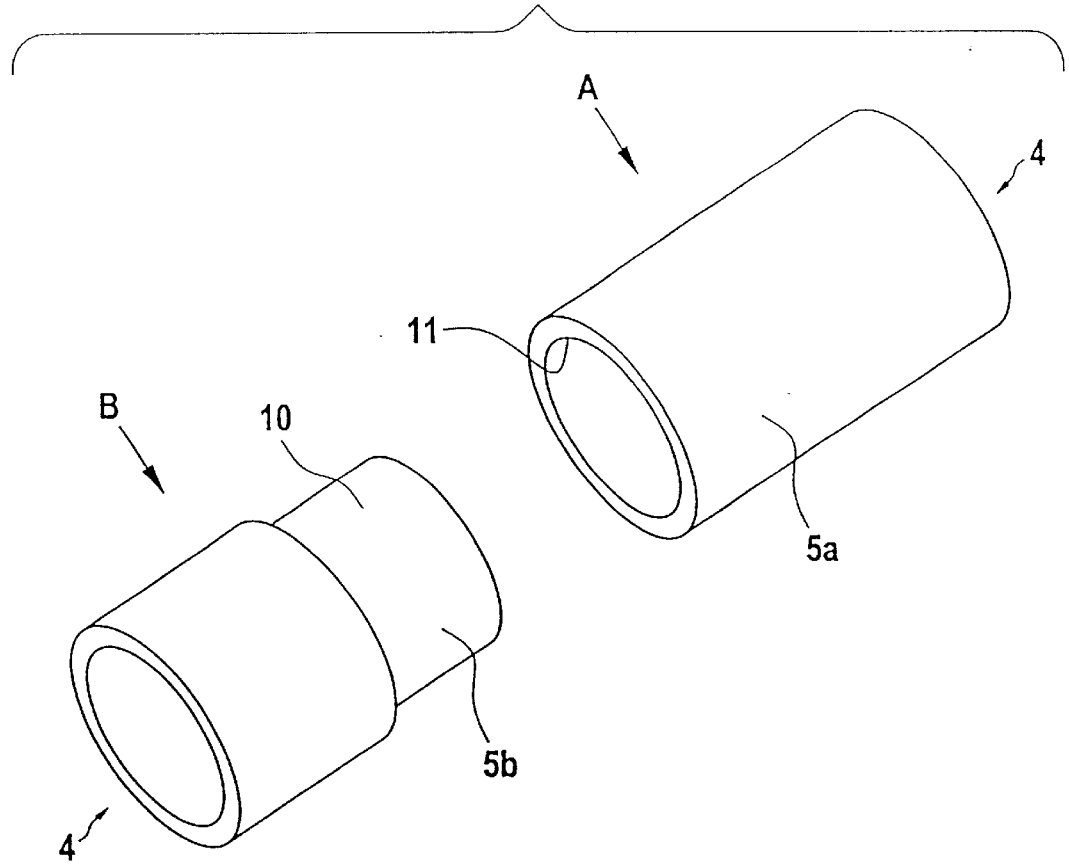
Figure 5A:
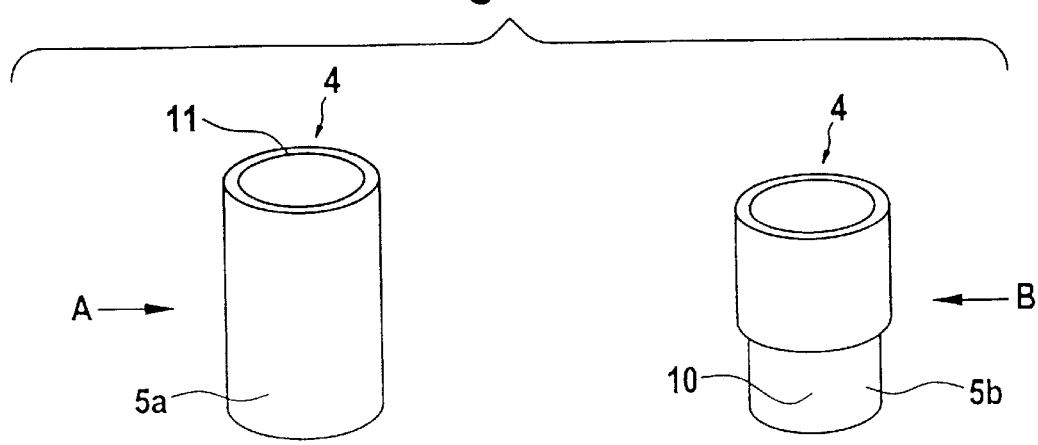
Figure 5B:
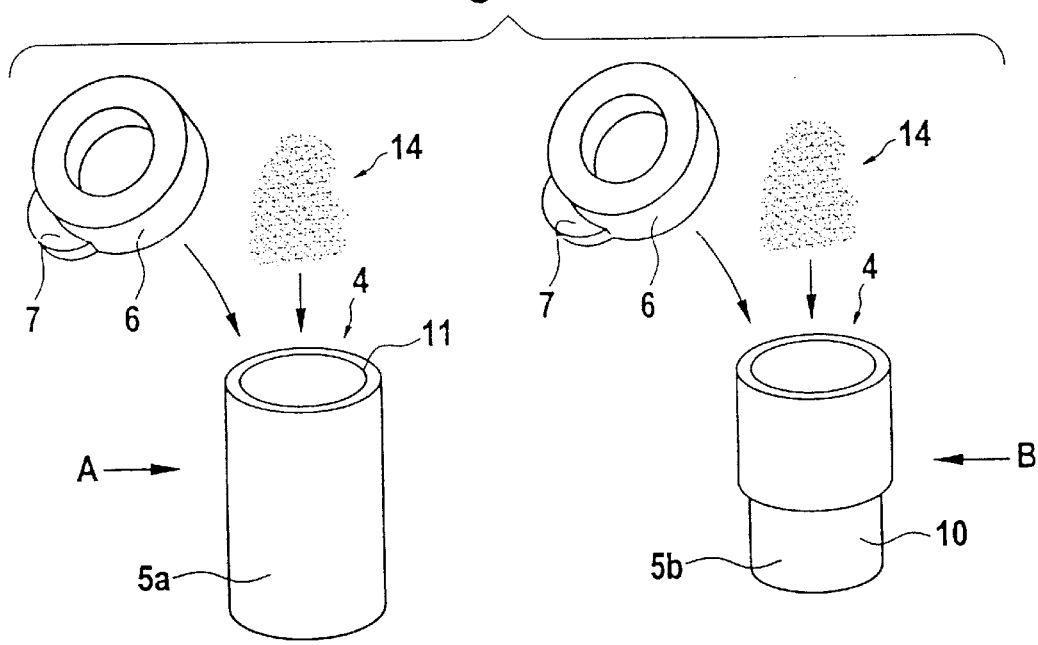
Figure 5C:
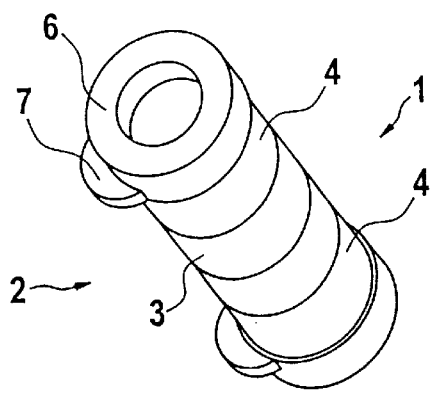

The invention is hereinafterwards described in embodiment examples by way of the drawings. These serve exclusively for the better illustration of individual embodiment forms according to the invention and are in no way of be considered as limiting. There are shown in:

FIG. 1 a perspective representation of a preferred embodiment of a container with the features of the invention, FIG. 2 a perspective representation of the two parts of a container with the features of the invention, FIG. 3 a longitudinal section through the two parts of a container with the features of the invention, FIG. 4 a longitudinal section through an alternative embodiment of a container with the features of the invention and FIGS. 5a–c a method for manufacturing a container with a filling product, with the features of the invention.

FIG. 1 shows the perspective representation of a particularly preferred embodiment of the invention. An elongate container 1 with a cylindrical base body 2, for example of opaque polypropylene comprises at both ends in each case a hollow space 4. The hollow spaces are connected to one another via an extension piece 3. The two hollow spaces 4 which are envisaged for receiving a predetermined quantity of filling product 14 are closed by in each case a snap lid 6 which for better handling comprises a projection 7.

Particularly proven is a base body 2 of 27 mm length and 11 mm diameter with a useable volume of 0.46 cm$^3$ per hollow space. The base body 2 consists of two parts A, B connected to one another.

FIG. 2 shows the two parts A, B which are connectable to one another and from which the base body 2 is put together. Each part A, B contains a hollow space 4 for the filling product 14 and a connection section 5a, 5b, wherein the outer wall 10 of the connection section 5b of the one part may be connected with a non-positive fit to the inner wall 11 of the connection section 5a of the other part A.

FIG. 3 shows a longitudinal section through the two parts which in each case contain a hollow space 4 for the filling of a predetermined quantity of filling product 14. The bottom 8 of both parts with this comprises in each case a curved transition section 9. The radius of curvature is approx. 2 mm. The outer diameter of the connection section 5b of part B is identical to the inner diameter of the connection section 5a of part A.

FIG. 4 shows an alternative embodiment example in the longitudinal section. Into a cylindrical base body 2' there are later applied bottoms 8' which via a flange or sealing bead 13 are latchable with a positive fit into a circumferential groove 12 of the base body 2'. By way of this there is achieved a compartmentisation of the base body 2' into two hollow spaces 4 for receiving a predeterminable quantity of filling product 14 and into an extension piece 3 lying therebetween which is not filled out. By way of a suitable dimensioning of the hollow spaces 4 the filling of small portions for the single or repeated application is achieved and by way of the extension piece 3 a good handling of the container 1 is achieved. It is particularly favourable when the insertable bottoms 8' are manufactured of a softer material than the base body 2'.

FIG. 5 shows a method for manufacturing a container according to the invention with a filling product.

In step a) two parts A, B are prepared which in each case comprise a hollow space 4 for receiving a predetermined quantity of filling product 14 as well as a connection piece 5a, 5b. It is particularly advantageous when each of the parts A, B are injected with the injection moulding method as one piece of a plastic, e.g. opaque polypropylene.

In step b) the hollow spaces 4 of the two parts A, B are filled with a predetermined quantity of filling product, in particular pasty tooth filler masses. The filling may with a suitable arrangement of the two parts A, B be carried out with a single filling unit. The filled hollow spaces 4 of the two parts A, B are subsequently closed. In order to permit a simple opening and in order to guarantee hygiene and where appropriate sterility of the filling product 14 preferably light-tight and moisture-tight reclosable snap lids 6 are used.

In step c) the filled and closed parts A, B are connected to one another such that the outer wall 10 of the connection section 5b of part B bears with a non-positive fit on the inner wall 11 of the connection section 5a of part A. The thus formed container by way of this comprises two oppositely lying hollow spaces 4 with a filling product 14, between which lies an extension piece 3.

What is claimed is:

1. A container having an approximately cylindrical body which defines a first hollow space, having a side wall and a bottom, for receiving a first quantity of a filling product and having an opening which may be closed by a recloseable closure, a second hollow space, having a side wall and a bottom, for receiving a second quantity of a filling product and having an opening which may be closed by a recloseable closure, an extension connecting the bottoms of the first and second hollow spaces, said second hollow space lying opposite said first hollow space in relation to said extension, and said openings being located on opposite sides of the container, so that each of said hollow spaces can be opened independently.

2. A container according to claim 1, wherein the extension is approximately in alignment with an outer surface of the cylindrical body.

3. A container according to claim 2, wherein the cylindrical body has a length of at least 20 mm.

4. A container according to claim 1, wherein the body comprises two parts which are connected to one another with a non-positive fit.

5. A container according to claim 4, wherein each of said two parts comprises a respective connection section, the connection sections being connectable to one another such that an outer wall of the connection section of one part bears against an inner wall of the connection section of the other part.

6. A container according to claim 5, wherein each of the two parts defines a closable hollow space for receiving a quantity of filling product, said space being separated by a bottom from the respective connection section.

7. A container according to claim 6, wherein each said bottom, via a curved transition section, blends into the outer wall.

8. A container according to claim 1, wherein the body comprises two parts which are connected to one another with a positive fit.

9. A container according to claim 8, wherein each of the two parts comprises a connection section, the respective connection sections being connectable to one another such that an outer wall of the connection section of one part bears against an inner wall of the connection section of the other part.

10. A container according to claim 9, wherein each of the two parts comprises a closable hollow space for receiving a quantity of the filling product, said space being separated by a bottom from the respective connection section.

11. A container according to claim 10, wherein each bottom, via a curved transition section, blends into the outer wall.

12. A container according to claim 1, wherein the useable volume of the closable hollow spaces is 0.2 cm$^3$ to 0.9 cm$^3$.

13. A container according to claim 1, wherein the recloseable closure is a snap lid.

14. A container according to claim 13, wherein said snap lid is light-tight and moisture-tight.

15. A container according to claim 13, wherein the snap lid comprises a projection projecting beyond the cylindrical body.

16. A container according to claim 1, wherein the hollow spaces contains a predetermined quantity of filling product.

17. A container according to claim 1, wherein said filling product is a pasty tooth filler mass.

18. A container according to claim 17, wherein the hollow spaces contains a predetermined quantity of filling product.

19. An integrated system comprising plural containers separably joined together each container having an approximately cylindrical body which defines a first hollow space for receiving a quantity of filling product, said first hollow space having an opening which is closed by a recloseable closure, and a second hollow space lying opposite a bottom of the first hollow space, for receiving a quantity of filling product and having an opening which is closed by a recloseable closure, and an extension connecting the bottoms of the first and second hollow spaces, so that said hollow spaces can be opened independently.

* * * * *